United States Patent

Cabri et al.

[11] Patent Number: 5,955,635
[45] Date of Patent: Sep. 21, 1999

[54] PROCESS FOR THE PREPARATION OF 4-(6'-METHOXY-2'-NAPHTHYL) BUTAN-2-ONE

[75] Inventors: Walter Cabri, Rozzano; Domenico Magrone, Milan; Roberto Angelini, Milan; Erminio Oldani, Milan, all of Italy

[73] Assignee: Secifarma S.P.A., Baranzate di Bollate, Italy

[21] Appl. No.: 09/065,972

[22] Filed: Apr. 24, 1998

[30] Foreign Application Priority Data

Apr. 30, 1997 [IT] Italy .................................. MI97A1006

[51] Int. Cl.$^6$ .................................................. C07C 45/45
[52] U.S. Cl. .............................................. 568/314; 560/53
[58] Field of Search ................................ 568/314; 560/53

[56] References Cited

U.S. PATENT DOCUMENTS 4,270,004  5/1981  Rose et al. ............................... 568/314
5,750,793  5/1998  Cannata et al. ......................... 568/314

*Primary Examiner*—James H. Reamer
*Attorney, Agent, or Firm*—Walter H. Schneider

[57] ABSTRACT

An improved process for the preparation of Nabumetone, which comprises the following steps:

a) condensation between 6-methoxy-naphthaldehyde I and t-butyl acetoacetate II, to give 3-t-butoxycarbonyl-4-(6'-methoxy-2'-naphthyl)-but-3-en-2-one III as an E/Z mixture;

b) hydrogenation of III in the presence of a palladium catalyst, to give 3-t-butoxycarbonyl-4-(6'-methoxy-2-naphthyl)-butan-2-one IV;

c) cleavage of the t-butyl ester by acid catalysis; and d) recrystallization of the crude with methanol.

2 Claims, No Drawings

PROCESS FOR THE PREPARATION OF 4-(6'-METHOXY-2'-NAPHTHYL) BUTAN-2-ONE

The present invention relates to a process for the preparation of 4-(6'-methoxy-2'-naphthyl)butan-2-one [nabumetone] V.

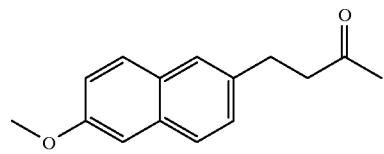

A number of naphthalene derivatives are known to be effective antiinflammatory drugs in the treatment of various rheumatic and arthritic diseases. Among the most investigated molecules, naproxen (J. Med. Chem. 1970, 13, 203) proved to be extremely successful in therapy. Nabumetone V represents the second generation of antinflammatories based on the naphthalene structure and is characterized by a decrease in side-effects, in particular a lower toxicity to the gastro-intestinal tract (BP 1474377).

Nabumetone V has been synthesized first in 1973 (Chatterjea, J. N. et al. *Indian J. Chem.* 1973, 214) and subsequently patented by Lake & Rose [U.S. Pat. No. 4,061,779 with GB 42550-73 priority of Sep. 11, 1973).

Different processes for the synthesis of Nabumetone have been described. The most competitive industrial processes are those starting from 6-methoxy-naphthaldehyde and acetoacetic acid esters.

U.S. Pat. No. 4,061,779 discloses the base-promoted condensation between 6-methoxy-naphthaldehyde I and acetone to give 4-(6-methoxy-2-naphthyl)-3-buten-2-one in a 41% yield (example 20). 4-(6-Methoxy-2-naphthyl)-3-buten-2-one is purified by chromatography on silica gel column as it is contaminated by different impurities due to the binding of other acetone molecules to the keto functionality. Nabumetone V is obtained by Pd/C catalyzed hydrogenation (example 21). Nabumetone V in the amorphous form, starting from 6-methoxy-naphthaldehyde, is obtained in a 29 mol % yield.

From the industrial point of view, the most competitive methods for the synthesis of Nabumetone V are based on the above cited condensation between 6-methoxy-naphthaldehyde I and acetoacetates, followed by hydrogenation and recrystallization. EP 3074 discloses the condensation of 6-methoxy-naphthaldehyde I with benzyl acetoacetate (example 1), the intermediate being then treated with Pd/C and hydrogen. The recrystallized crude compound gives solid Nabumetone V in a 67% yield (M.p. 81° C.). Similar results concerning the use of benzyl acetoacetates substituted on the aromatic ring (examples 4, 5, 6) were described. Esters cleavable by hydrogenation are claimed.

EP 3074 also discloses the reaction between 6-methoxy-naphthaldehyde I and ethyl acetoacetate. In this case, the total yield of the process is of only 37–41% (description 10). The method based on acetoacetic acid benzyl esters is, in fact, described in the Patent as an improvement of the method which makes use of ethyl acetoacetate.

It has surprisingly been found that the use of t-butyl acetoacetate II in the reaction with 6-methoxy-naphthaldehyde I provides, after hydrogenation and recrystallization-deprotection, Nabumetone I in only three steps, in a high yield (65–70%).

The process of the invention is illustrated in the following reaction scheme:

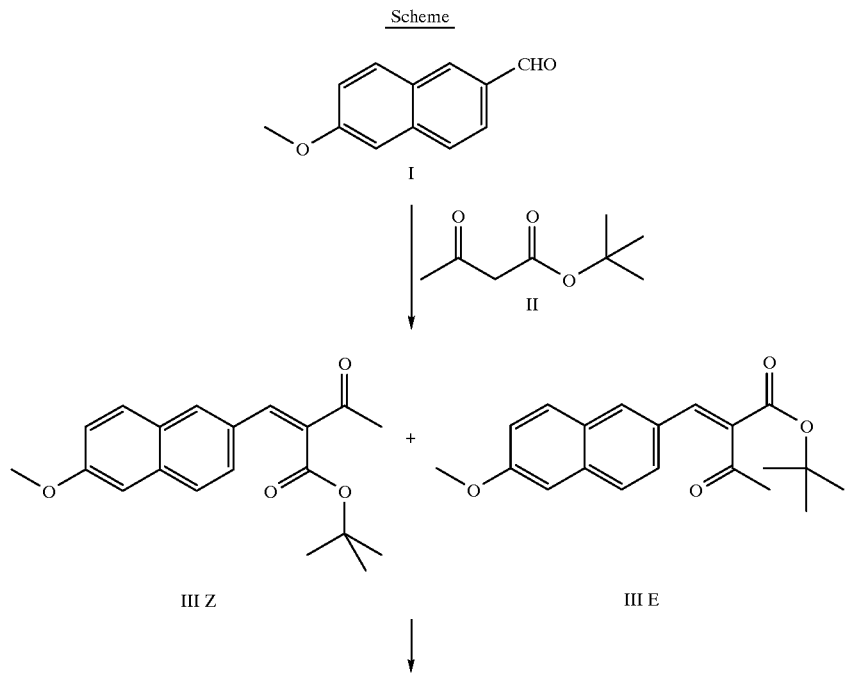

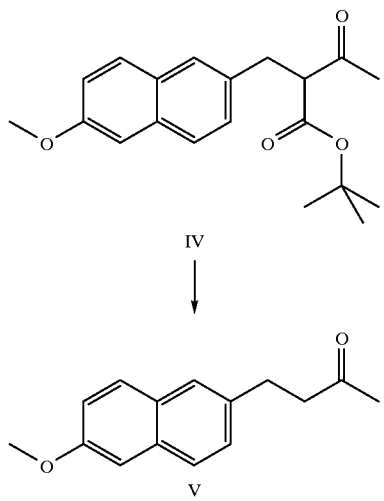

t-Butyl acetoacetate is an inexpensive starting product and remarkably lower amounts of palladium catalyst than those reported in the process claimed in EP 3074 are necessary for the hydrogenation of the double bond in heterogeneous phase.

The condensation between 6-methoxy-naphthaldehyde I and t-butyl acetoacetate II is carried out in the presence of a catalyst, typically an organic salt of a secondary amine such as piperidine acetate, pyrrolidine acetate or the corresponding phenyl acetates, in an apolar solvent such as cyclohexane, heptane or hexane, cyclohexane being preferred. The reaction reaches completion in some hours under reflux. The compound, 3-t-butoxycarbonyl-4-(6'-methoxy-2'-naphthyl)-but-3-en-2-one III, is recovered as an E/Z mixture in a yield ranging from 80 to 85%. III Proves to be stable to acids, although a number of methods for the acid deprotection of t-butyl esters are described (G. W. Anderson and F. M. Callahan, *J.A.C.S.* 1960, 82, 3359; S. Chandrasekaran, A. F. Kluge, and J. A. Edwards, *J.O.C.* 1977, 42, 3972; D. B. Bryan, R. F. Hall, K. G. Holden, W. F. Huffman, and J. G. Gleason, *J.A.C.S.* 1977, 99, 2353).

The subsequent hydrogenation, carried out in tetrahydrofuran with 1–3% by weight of 5% palladium catalyst containing 50% of water, gives 3-t-butoxycarbonyl-4-(6'-methoxy-2'-naphthyl)-butan-2-one IV in a quantitative yield.

Nabumetone V can then be obtained by cleavage of the t-butyl ester with acid catalysis in an aromatic solvent and recrystallization of the crude with methanol (81% yield).

The preferred, most efficient procedure comprises the cleavage of the ester and the recrystallization in a single step, using $H_2SO_4$ as acid in alcohol, under reflux, in anhydrous medium. Isopropanol is the most preferred alcohol. The reaction is complete in some hours and compound V is obtained pure, by simple cooling, in a 65–70% yield, starting from 6-methoxy-naphthaldehyde I.

EXAMPLE 1

Synthesis of (E/Z) 3-t-Butoxycarbonyl-4-(6'-Methoxy-2'-Naphthyl)-But-3-En-2-One III E/III Z The mixture of 6-methoxy-2-naphthaldehyde I (37.24 g, 0.2 mols), t-butyl acetoacetate II (47.46 g, 0.3 mols), cyclohexane (320 ml) and piperidine acetate (1.45 g, 0.01 mols) is refluxed, removing water with a Dean-Stark apparatus. After 2 hours, temperature is brought to 60° C. and 56.8 ml of tetrahydrofuran are added. The mixture is left to cool to room temperature, then stirred at said temperature overnight. The precipitate is filtered and washed with cyclohexane, the resulting solid is dried. Mother liquors are concentrated to obtain a second crop. 52.5 g of mixture IIIE/IIIZ are recovered—Molar yield 81%—HPLC purity: >99%.

The reaction is repeated with 2 mols of 6-methoxy-2-naphthaldehyde I to give a 69 mol % yield.

EXAMPLE 2

Synthesis of 3-t-Butoxycarbonyl-4-(6'-Methoxy-2'-Naphthyl)-Butan-2-One IV

The mixture IIIE/IIIZ (25 g) is dissolved in ml 125 of tetrahydrofuran, then 5% Pd/C containing 50% of water (0.25 g, 1% by weight on the product) is added. The mixture is stirred in autoclave under hydrogen at 50° C. for 5 hours. The catalyst is filtered off, then the solvent is evaporated to dryness. 25 g of IV are obtained—Molar yield 99.4%—HPLC purity: >97%—M.p.: 63.6° C.

EXAMPLE 3a

Synthesis of 4-(6'-Methoxy-2'-Naphthyl)Butan-2-One V

The solution of compound IV (11 g) in isopropanol (66 ml) is added with conc. sulfuric acid (0.67 ml). After 5 hours under reflux, the reaction mixture is cooled to 15° C. and filtered. The resulting precipitate is washed with isopropanol and cold methanol, then dried to obtain 6.2 g of V—Molar yield 82%—HPLC purity: >99.5%—M.p.: 81–82° C.

EXAMPLE 3b

Synthesis of 4-(6'-Methoxy-2'-Naphthyl)Butan-2-One V

The solution of compound IV (11 g) in toluene (66 ml) is added with paratoluenesulfonic acid hydrate (0.318 g).

After 3 hours under reflux, the reaction mixture is cooled to room temperature, washed with water and evaporated to dryness. The resulting residue is crystallized from methanol, filtered and then dried. 6.1 g of Nabumetone V are obtained—Molar yield 80%—HPLC purity: >99.5%—M.p.: 81–82° C.

We claim:

1. A process for the-preparation of 4-(6'-methoxy-2'-naphthyl)butan-2-one (V) which comprises the following steps:

a. Condensation between 6-methoxy-naphthaldehyde (I) and t-butyl acetoacetate (II) in an apolar solvent selected from cyclohexane, heptane and hexane and in the presence of a catalyst comprising an organic salt of a secondary amine selected from piperidine acetate, pyrrolidine acetate and the corresponding phenyl acetates to give 3-t-butoxycarbonyl-4-(6'-methoxy-2'-naphthyl)-but-3-en-2-one (III) as an E/Z mixture;

b. hydrogenation of (III) in tetrahydrofuran in the presence of 1–3% by weight of 5% palladium catalyst ccontaining 50% water to give 3-t-butoxycarbonyl-4-(6'-methoxy-2'-naphthyl)-butan-2-one (IV);

c. cleavage of (IV) by acid catalysis in an aromatic solvent to give crude (I); and d. recrystallization of crude (I) with methanol.

2. A process according to claim 1 in which the cleavage and recrystallization steps are carried as a single combined step using $H_2SO_4$ in isopropanol under reflux in an anhydrous medium.

* * * * *